US012765809B2

(12) United States Patent
Choi et al.

(10) Patent No.: US 12,765,809 B2
(45) Date of Patent: Oct. 20, 2026

(54) SENSOR UNIT FOR MEASURING BIOMETRIC INFORMATION

(71) Applicant: I-SENS, INC., Seoul (KR)

(72) Inventors: Hyun Ho Choi, Seoul (KR); Goang Yel Ryu, Seoul (KR); Ji Hoon Wang, Seoul (KR)

(73) Assignee: I-SENS, INC., Seoul (KR)

( * ) Notice: Subject to any disclaimer, the term of this patent is extended or adjusted under 35 U.S.C. 154(b) by 223 days.

(21) Appl. No.: 18/575,248

(22) PCT Filed: Nov. 11, 2021

(86) PCT No.: PCT/KR2021/016416
§ 371 (c)(1),
(2) Date: Dec. 28, 2023

(87) PCT Pub. No.: WO2023/277270
PCT Pub. Date: Jan. 5, 2023

(65) Prior Publication Data

US 2024/0315608 A1 Sep. 26, 2024

(30) Foreign Application Priority Data

Jun. 29, 2021 (KR) ........................ 10-2021-0084616

(51) Int. Cl.
*A61B 5/145* (2006.01)
*A61B 5/00* (2006.01)

(52) U.S. Cl.
CPC ...... *A61B 5/14532* (2013.01); *A61B 5/14503* (2013.01); *A61B 5/68335* (2017.08);
(Continued)

(58) Field of Classification Search
CPC ............ A61B 5/14532; A61B 5/14503; A61B 5/68335; A61B 2560/0412;
(Continued)

(56) References Cited

U.S. PATENT DOCUMENTS 7,381,184 B2 * 6/2008 Funderburk ....... A61B 5/14503 604/59
10,194,842 B2 * 2/2019 Peterson .............. A61B 5/7405
(Continued)

FOREIGN PATENT DOCUMENTS

CN 112512420 3/2021
EP 1177802 2/2002
(Continued)

OTHER PUBLICATIONS

Extended European Search Report dated Feb. 24, 2025 for European Patent Application No. 21948570.3.
(Continued)

*Primary Examiner* — Navin Natnithithadha
(74) *Attorney, Agent, or Firm* — WOMBLE BOND DICKINSON (US) LLP

(57) ABSTRACT

The present invention provides a sensor unit in which a sensor inserted into a user's skin along with a needle can be kept being stably inserted into the skin without being affected by the movement of the needle in the process of the needle being separated from the user's skin. The sensor unit according to the present invention, which is attached to the user's skin to measure the user's biometric information, comprises: a sensor that includes a sensor body and an insertion part connected to the sensor body so as to be placed on a different plane from the sensor body and capable of being inserted into the user's skin; a housing base that includes a housing base hole through which the insertion part passes, and supports the sensor body; a housing cap that is coupled to the housing base and covers the sensor body; and a retention protrusion that protrudes from the housing cap to contact the sensor in order to prevent the insertion part from moving backward toward the housing cap.

7 Claims, 15 Drawing Sheets

(52) U.S. Cl.
CPC . *A61B 2560/0412* (2013.01); *A61B 2560/045* (2013.01); *A61B 2560/0462* (2013.01); *A61B 2562/227* (2013.01)

(58) Field of Classification Search
CPC ...... A61B 2560/045; A61B 2560/0462; A61B 2562/227; A61B 2560/0443; A61B 5/6849; A61B 2562/242; A61B 5/6833; A61B 2090/034; A61B 2562/16; A61M 2005/1585
See application file for complete search history.

(56) References Cited

U.S. PATENT DOCUMENTS

| | | | | |
|---|---|---|---|---|
| 10,194,843 | B2 * | 2/2019 | Peterson | A61B 5/686 |
| 10,327,679 | B2 * | 6/2019 | Peterson | A61B 5/14503 |
| 10,335,066 | B2 * | 7/2019 | Peterson | A61B 5/1473 |
| 10,376,187 | B2 * | 8/2019 | Peterson | A61B 5/7405 |
| 10,456,064 | B2 * | 10/2019 | Peterson | A61B 5/14503 |
| 11,399,747 | B2 * | 8/2022 | Huang | A61B 5/0004 |
| 2009/0093696 | A1 | 4/2009 | Say et al. | |
| 2009/0234212 | A1 * | 9/2009 | Slomski | A61B 5/6849 600/345 |
| 2016/0058344 | A1 * | 3/2016 | Peterson | A61B 5/686 600/347 |
| 2016/0058470 | A1 * | 3/2016 | Peterson | A61B 5/6848 600/365 |
| 2016/0058471 | A1 * | 3/2016 | Peterson | A61B 5/686 600/347 |
| 2016/0058472 | A1 * | 3/2016 | Peterson | A61B 5/0004 600/347 |
| 2016/0058473 | A1 * | 3/2016 | Peterson | A61B 5/14503 600/347 |
| 2016/0058474 | A1 * | 3/2016 | Peterson | A61B 5/686 600/347 |
| 2017/0202497 | A1 * | 7/2017 | Yee | A61B 5/14865 |
| 2020/0138353 | A1 | 5/2020 | Yee et al. | |
| 2021/0030325 | A1 | 2/2021 | Huang et al. | |
| 2021/0259595 | A1 * | 8/2021 | Chae | A61B 5/14532 |
| 2021/0267503 | A1 * | 9/2021 | Chae | A61B 5/14532 |
| 2021/0267504 | A1 * | 9/2021 | Chae | A61B 5/14532 |
| 2021/0267511 | A1 * | 9/2021 | Chae | A61B 5/14532 |
| 2021/0290116 | A1 * | 9/2021 | Chae | A61B 5/14532 |
| 2021/0290117 | A1 * | 9/2021 | Chae | A61B 5/14532 |
| 2022/0031206 | A1 * | 2/2022 | Jeong | A61B 5/6849 |
| 2022/0257153 | A1 * | 8/2022 | Jeong | A61B 5/14532 |

FOREIGN PATENT DOCUMENTS

| | | |
|---|---|---|
| EP | 4 344 624 | 4/2024 |
| JP | 2010-227601 | 10/2010 |
| JP | 2020-520284 | 7/2020 |
| JP | 2021-23818 | 2/2021 |
| KR | 10-1128305 | 3/2012 |
| KR | 10-2012-0047896 | 5/2012 |
| KR | 10-2020-0036121 | 4/2020 |
| KR | 10-2200142 | 1/2021 |
| KR | 10-2021-0016306 | 2/2021 |
| WO | 99/56613 | 11/1999 |
| WO | 2017/116915 | 7/2017 |
| WO | 2018/215421 | 11/2018 |

OTHER PUBLICATIONS

Office Action (1st) dated Sep. 30, 2025 for Japanese Patent Application No. 2023-580848 and its English translation from Global Dossier.

International Search Report for PCT/KR2021/016416 mailed on Mar. 23, 2022 and its English translation from WIPO (now published as WO 2023/277270).

Written Opinion of the International Searching Authority for PCT/KR2021/016416 mailed on Mar. 23, 2022 and its English machine translation from WIPO (now published as WO 2023/277270).

Office Action dated Dec. 9, 2025 for Canadian Patent Application No. 3,224,160.

Extended European Search Report dated Jul. 9, 2026 for European Patent Application No. 26181321.6.

Office Action dated Aug. 31, 2026 for New Zealand Patent Application No. 807054.

* cited by examiner

SENSOR UNIT FOR MEASURING BIOMETRIC INFORMATION

CROSS-REFERENCE TO RELATED APPLICATIONS

The present application is the U.S. National Phase of PCT Application No. PCT/KR2021/016416 filed on Nov. 11, 2021, which claims the priority to Korean Patent Application No. 10-2021-0084616 filed on Jun. 29, 2021, the entire contents of which are incorporated herein by reference.

TECHNICAL FIELD

The present disclosure relates to a sensor unit for biometric information measurement, and more specifically, to a sensor unit for biometric information measurement that is attached to the skin of a user and can measure the biometric information of a user.

BACKGROUND

With the recent advancement of medical technology, various medical devices that are attached to the body of a user have been developed and sold. Medical devices that are attached to the skin can be useful for monitoring biometric information or providing treatment by attaching them to the body of a patient with a chronic disease.

For example, chronic diseases such as diabetes require continuous management, and a body attachable unit for biometric information measurement that is attached to the body can be used to manage blood glucose levels in diabetic patients.

Diabetes is characterized by substantial absence of subjective symptoms at the beginning of the condition, when diabetes progresses, diabetes-specific symptoms such as overdrink, overeat, polyuria, weight loss, weariness, skin itchiness, and lower ability of naturally healing on injury on hands and feet are shown. Further progression of diabetes leads to complications such as visual disturbances, hypertension, kidney disease, paralysis, periodontal disease, muscle spasms and neuralgia, as well as gangrene.

In order to diagnose diabetes beforehand and manage to prevent the progression of diabetes into complications associated therewith, systematic blood glucose measurement and treatment should be performed.

For diabetes patients as well as people having higher than normal blood glucose, even though diabetes has not yet developed, medical device manufacturers offer a variety of blood glucose meters to measure blood glucose levels.

Glucose measuring devices may be categorized into a single time measurement type measuring a blood glucose level and collecting blood from a fingertip by a user every single time and a continuous measurement type attaching a glucose monitoring system to the belly or an arm of the user and continuously measuring blood glucose levels.

Diabetics patients generally experience hyperglycemia and hypoglycemia, an emergency may occur in the hypoglycemic conditions, and the patients may become unconscious or die if a hypoglycemic condition lasts for an extended period of time without the supply of glucose. Accordingly, although rapid discovery of the hypoglycemic condition is critically important for diabetics, blood-collecting type glucose monitoring devices intermittently measuring glucose have limited ability to accurately measure blood glucose levels.

Recently, to overcome such a drawback, continuous glucose monitoring systems (CGMSs) inserted into the human body to measure a blood glucose level every few minutes have been developed, and therefore easily perform the management of diabetics and responses to an emergency situation.

A continuous blood glucose measurement system includes a sensor unit that includes a transcutaneous sensor that is inserted into the skin of a user and measures blood glucose levels in the body, a base unit that is electrically connected to the sensor unit and generates a signal from biometric information measured by the sensor, and a terminal that receives and outputs a signal transmitted from the base unit.

An applicator is used to insert the sensor into the body. The applicator includes a needle that is inserted into the skin of a user along with a sensor to insert the sensor into the skin of a user. The needle is removed from the skin of a user after the sensor is inserted into the skin of a user.

However, in the process of removing the needle inserted into the skin of a user along with the sensor, the sensor may be affected by the movement of the needle, causing a problem of partially coming out of the skin of a user. If the sensor partially comes out of the skin, this will lead to a problem in which the measurement accuracy of the sensor decreases.

SUMMARY

Technical Problem

The present disclosure is developed in consideration of the above-mentioned points, and the purpose is to provide a sensor unit that allows a sensor inserted into the skin of a user along with a needle to remain stably inserted into the skin without being affected by the movement of the needle during the process of separating the needle from the skin of a user.

Solution to Problem

To accomplish the above-described purposes, a sensor unit for measuring biometric information of a user by being attached to skin of a user according to an embodiment of the present disclosure may comprise: a sensor comprising a sensor body, and an insertion portion connected to the sensor body to be disposed on a plane different from the sensor body to be inserted into the skin of the user; a housing base having a housing base hole through which the insertion portion passes, and supporting the sensor body; a housing cap coupled to the housing base and covering the sensor body; and a retention protrusion protruding from the housing cap to be contacted with the sensor to prevent movement of the insertion portion retreating toward the housing cap.

The sensor connects the sensor body and the insertion portion by being disposed on the plane different from the sensor body and comprises a middle portion wider than the insertion portion, and the retention protrusion may be provided to contact the middle portion.

The housing base may have a support portion disposed inside the housing base hole to support the middle portion.

The housing base comprises a base portion supporting the sensor body and a boss protruding from the base portion, and the housing base hole is formed to penetrate the boss in the base portion, and the support portion may be disposed inside the boss.

The sensor comprises a connection portion connecting the sensor body and the middle portion, the middle portion has a first extension portion protruding from one side of the connection portion, and a second extension portion protruding from the extension portion in a direction opposite to a direction in which the first extension portion protrudes from the connection portion, the insertion portion is connected to the first extension portion, and the retention protrusion may be arranged to contact the second extension portion.

The housing cap may have a protrusion pressing the sensor body toward the housing base by being contacted with the sensor body.

The sensor unit according to an embodiment of the present disclosure may further comprise an adhesive pad interposed between the sensor body and the housing cap to adhere the sensor body and the housing cap.

The sensor unit according to an embodiment of the present disclosure may further comprise a sensor adhesive portion interposed between the sensor body and the housing base to attach one surface of the sensor body to the housing base, and the sensor adhesive portion has a sensor adhesive portion opening, the sensor body has a contact point disposed in the sensor adhesive portion opening for electrical connection, and the sensor adhesive portion seals the contact point by surrounding the contact point.

Advantageous Effects of Invention

According to the present disclosure, in a state in which a sensor is mounted on the sensor unit housing, the retention protrusion of the sensor unit housing contacts the sensor to restrict the movement of the sensor. Therefore, the insertion portion of the sensor inserted into the skin of a user can be stably maintained in a state of protruding from the sensor unit housing by a certain length. In addition, in a state in which the insertion portion of the sensor is inserted into the skin of a user, it is possible to maintain a state inserted into the skin of a user at a certain depth without retreating from the skin of a user.

In addition, according to the present disclosure, after the insertion portion of the sensor is inserted into the skin of a user with the needle, in the process of the needle coming out of the skin of a user, the retention protrusion supports to prevent the sensor from moving, thereby preventing the insertion portion from retracting in the same direction as the needle. In addition, the insertion portion partially escapes the skin, thereby reducing the problem of poor measurement accuracy of the sensor.

DETAILED DESCRIPTION OF EMBODIMENTS

Figure 1:
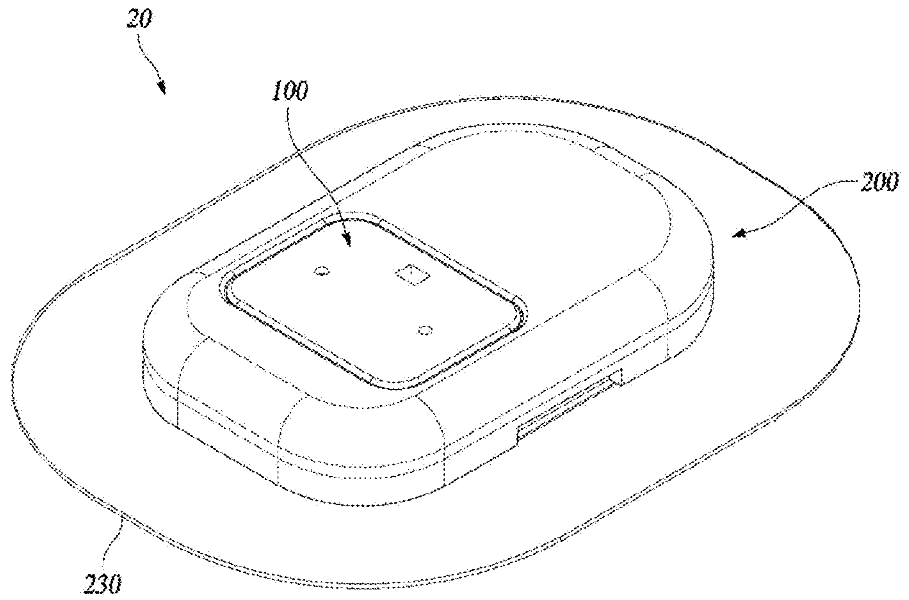
FIG. 1 is a perspective view showing a body attachable unit according to an embodiment of the present disclosure.
Figure 2:
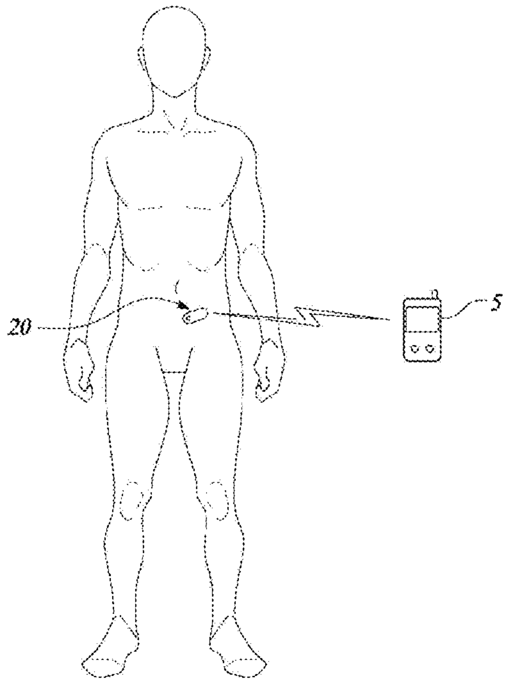
FIG. 2 shows a body attachable unit according to an embodiment of the present disclosure attached to the skin of a user.

Hereinafter, the sensor unit for biometric information measurement according to the present disclosure will be described in detail with reference to the drawings.

The sensor unit (100) according to an embodiment of the present disclosure is coupled with the base unit (200) including electronic components to form a body attachable unit (20), and can be attached to the skin of a user while coupled with the base unit (200) to measure biometric information. The base unit (200) may be configured with an electronic component installed therein. This base unit (200) is electrically connected to the sensor unit (100) and can process biometric information measured by the sensor unit (100) and transmit it to the external terminal (5). The external terminal (5) may be a variety of devices capable of receiving measurement data from the body attachable unit (20), such as a portable terminal, a medical device, a PC, or a server. Biometric information that the sensor unit (100) can measure is not limited to specific information. For example, the sensor unit (100) may periodically measure the user's blood glucose level. The body attachable unit (20) may be attached to the skin of a user by an applicator (30).

Figure 3:
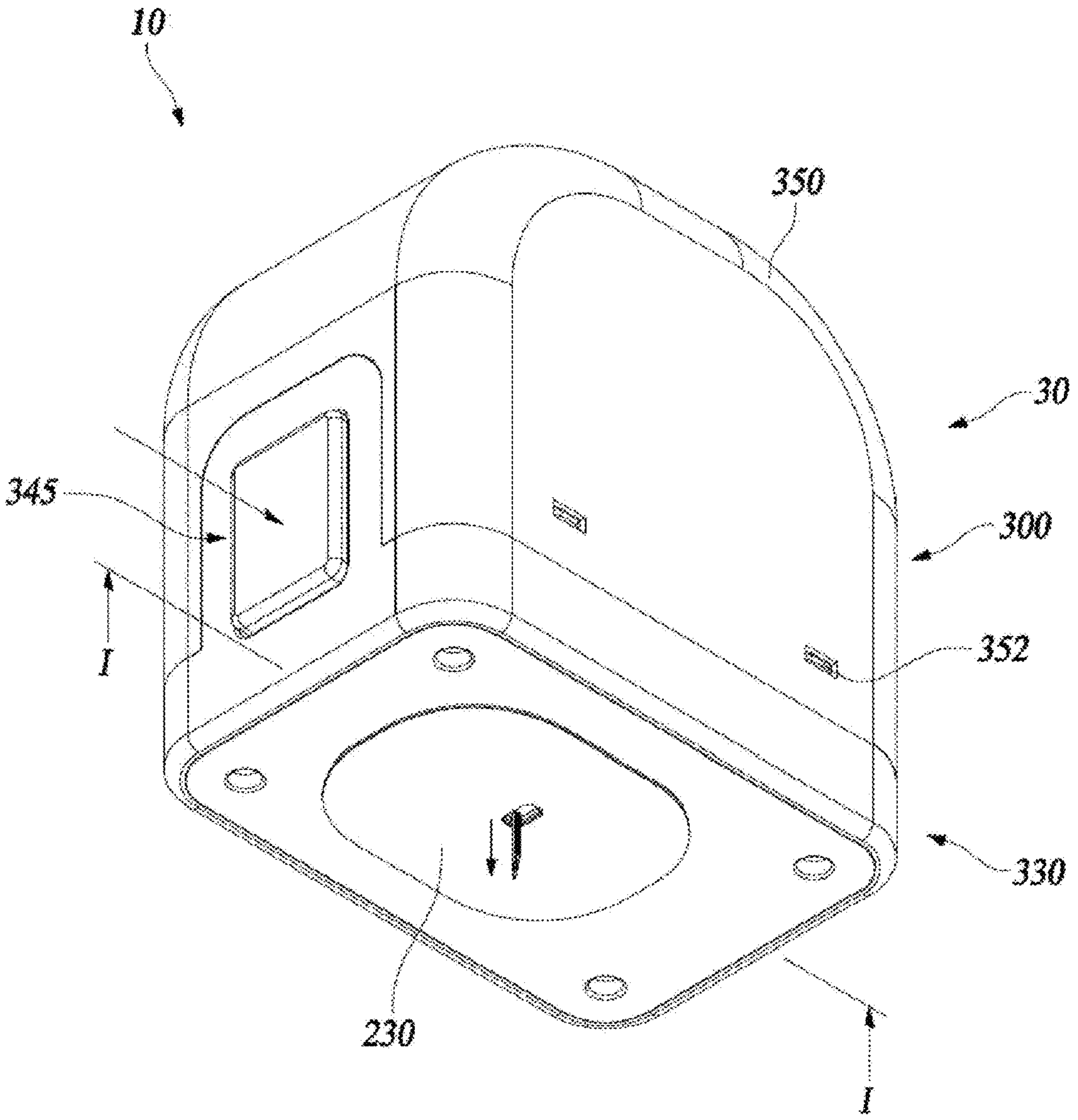
FIG. 3 is a perspective view showing an applicator assembly including an applicator for attaching a body attachable unit according to an embodiment of the present disclosure to the skin of a user.
Figure 4:
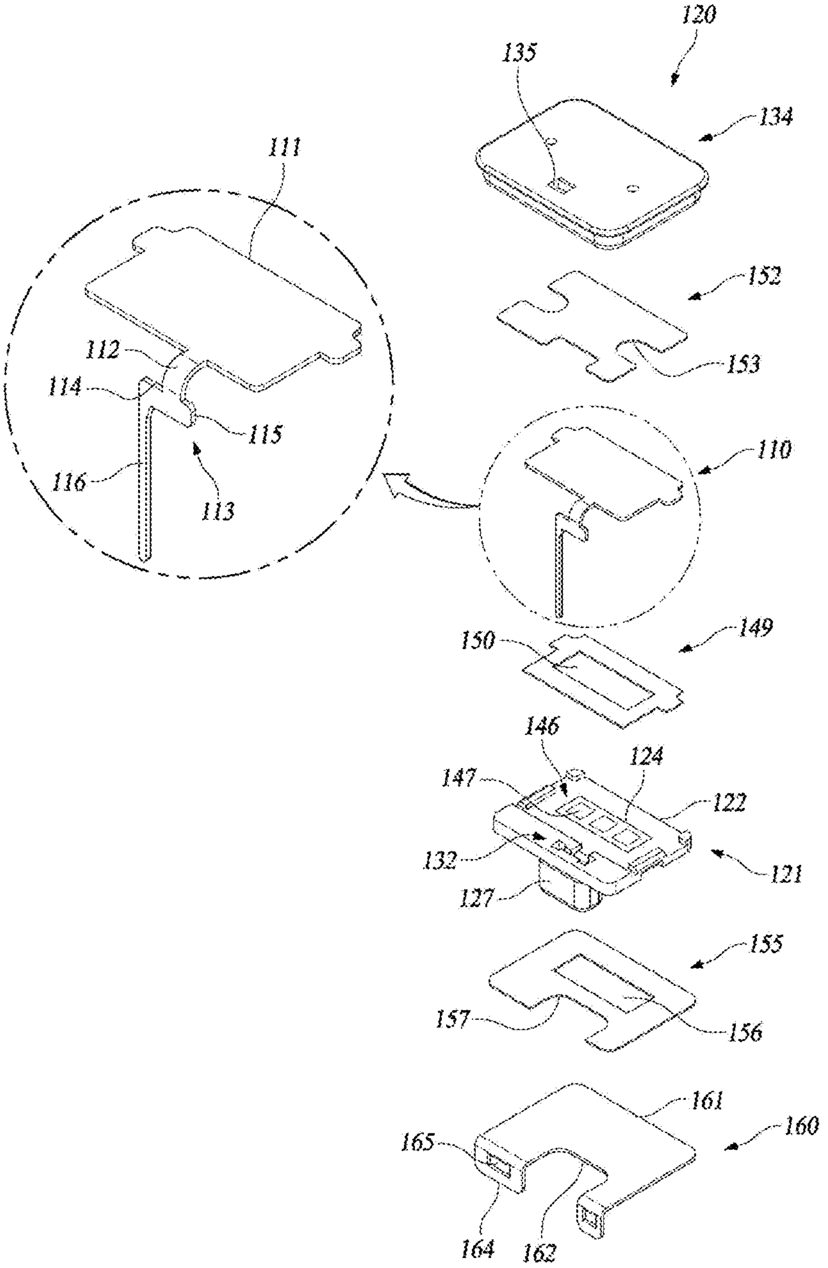
FIGS. 4 and 5 are exploded perspective views showing a sensor unit.
Figure 5:
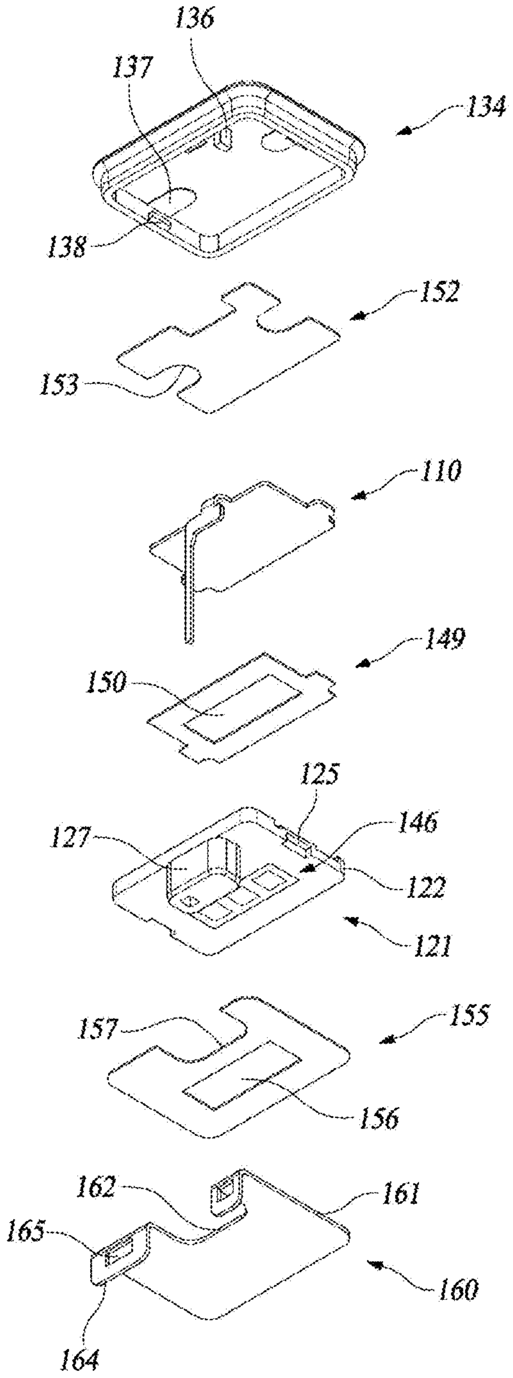

FIG. 3 is a perspective view showing an applicator assembly including an applicator for attaching a body attachable unit according to an embodiment of the present disclosure to the skin of a user.

The applicator assembly (10) includes a sensor unit (100), a base unit (200), and an applicator (30). The applicator assembly (10) may be provided to the user with the sensor unit (100) and the base unit (200) mounted separately on the applicator (30). The sensor unit (100) and the base unit (200) can be automatically assembled and attached to the skin of a user through the action of the applicator (30).

Referring to FIGS. 4 to 13, the sensor unit (100) includes a sensor (110) inserted into the skin of a user, a sensor unit housing (120) to which the sensor (110) is coupled, a sensor unit-electrical contact portion (146) coupled to the sensor unit housing (120) and electrically connected to the sensor (110), an adhesive portion (149) and adhesive pad (152) for fixing the sensor (110) to the sensor unit housing (120), an adhesive layer (155) provided on the sensor unit housing (120) so as to be attached to the base unit (200), and protective sheet (160) covering the adhesive layer (155).

The sensor (110) includes a sensor body (111), a connection part (112) connected to one side of the sensor body (111), a middle portion (113) connected to the sensor body (111) through the connection portion (112) and an insertion portion (116) connected to the middle portion (113) so as to be inserted into the skin of a user. The sensor body (111) is disposed inside the sensor unit housing (120) so as to be in contact with the sensor unit-electrical contact portion (146). The sensor body (111) may be provided with an electrode electrically connected to the sensor unit-electrical contact portion (146). The connection portion (112) extends from the edge of the sensor body (111) and connects the sensor body (111) and the middle portion (113) to lie on different planes. The sensor (110) may be manufactured in a flat form in which the sensor body (111) lies on the same plane as the middle portion (113) and the insertion portion (116), and then manufactured in a form in which the connection portion (112) is bent and deformed so that the sensor body (111) lies on a different plane from the middle portion (113) and the insertion portion (116).

The middle portion (113) and the insertion portion (116) are connected to the sensor body (111) so as to lie on a different plane from the sensor body (111). In the drawing, the middle portion (113) and the insertion portion (116) are shown to be disposed on the same plane, and the middle portion (113) is disposed perpendicular to the sensor body (111), but the angle between the middle portion (113) and the sensor body (111) or the angle between the insertion portion (116) and the sensor body (111) can be changed in various ways.

The middle portion (113) includes a first extension portion (114) that protrudes to one side of the connection portion (112), and a second extension portion (115) that protrudes from the connection portion (112) in a direction opposite to the direction in which the first extension portion (114) protrudes from the connection portion (112). The insertion portion (116) may be connected to the first extension portion (114) and inserted into the skin of a user. The insertion portion (116) has a relatively thin and long shape so as to be smoothly inserted into the skin of a user. The connection portion (112), the middle portion (113), and the insertion portion (116) may be provided with a conductive trace electrically connected to the electrode of the sensor body (111). The sensor (110) may be coupled to the sensor unit housing (120) so that the sensor body (111), the connection portion (112) and the middle portion (113) are located inside the sensor unit housing (120) and only the insertion portion (116) protrudes from the sensor unit housing (120).

The sensor unit housing (120) includes a housing base (121) and a housing cap (134) that covers the top of the housing base (121). A space is provided inside the sensor unit housing (120) to accommodate the sensor (110), and a housing opening (140) into which a needle (450) for inserting the sensor (110) into the skin of a user is inserted is formed in the middle of the sensor unit housing (120) to penetrate the sensor unit housing (120) in the thickness direction.

The housing base (121) includes a base portion (122) supporting the sensor body (111) of the sensor (110), and a boss (127) protruding from the surface of the base portion (122). On one side of the base portion (122), a base portion hole (123) is formed to penetrate the base portion (122), and on the other side of the base portion (122), a through hole (124) is formed to penetrate the base portion (122). A sensor unit-electrical contact portion (146) is coupled to the through hole (124). A detent groove (125) is provided at the edge of the base portion (122).

The boss (127) protrudes from the surface on the side of the base portion (122) on which the sensor (110) is not placed. A boss hole (128) is formed in the boss (127) to penetrate the boss (127). The boss hole (128) is connected to the base portion hole (123) and forms a housing base hole (132) together with the base hole (123). The boss hole (128) includes an upper hole (129) connected to the base portion hole (123) and a lower hole (130) connected to the upper hole (129) and extending to the end of the boss (127). The size of the upper hole (129) is larger than the size of the lower hole (130). The upper hole (129) is sized to accommodate the middle portion (113) of the sensor (110) and portion of the needle (450), and the lower hole (130) is sized to accommodate the insertion portion (116) of the sensor (110) and a portion of the needle (450). The upper hole (129) is provided with a support portion (131) capable of supporting the middle portion (113) of the sensor (110). As the support portion (131) supports the middle portion (113), the sensor (110) does not move while coupled to the sensor unit housing (120) and can maintain a stable coupling state with the sensor unit housing (120).

The housing cap (134) is coupled to the housing base (121) and covers the sensor body (111) of the sensor (110) placed on the housing base (121) and the upper part of the housing base (121). A housing cap hole (135) is formed in the middle of the housing cap (134) to penetrate the housing cap (134) in the thickness direction. The housing cap hole (135) is connected to the housing base hole (132) of the housing base (121) to form the housing opening (140). The needle (450) for inserting the sensor (110) into the skin of a user is inserted along with the sensor (110) into the housing opening (140). The housing cap (134) is provided with a detent protrusion (138) corresponding to the detent groove (125) of the housing base (121). The housing cap (134) may be coupled to the housing base (121) by inserting the detent protrusion (138) into the detent groove (125) and engaging the housing base (121). A protrusion (137) and a retention protrusion (136) are provided on the inner surface of the housing cap (134) facing the housing base (121). The protrusion (137) and the retention protrusion (136) protrude toward the housing base (121). The protrusion (137) and the retention protrusion (136) may contact the sensor (110) to prevent movement of the sensor (110) and stably fix the sensor (110) to the sensor unit housing (120). The protrusion (137) may contact the sensor body (111) of the sensor (110) and press the sensor body (111) toward the housing base (121). Therefore, the sensor body (111) can remain stably fixed to the housing base (121) without being lifted from the housing base (121).

Figure 6:
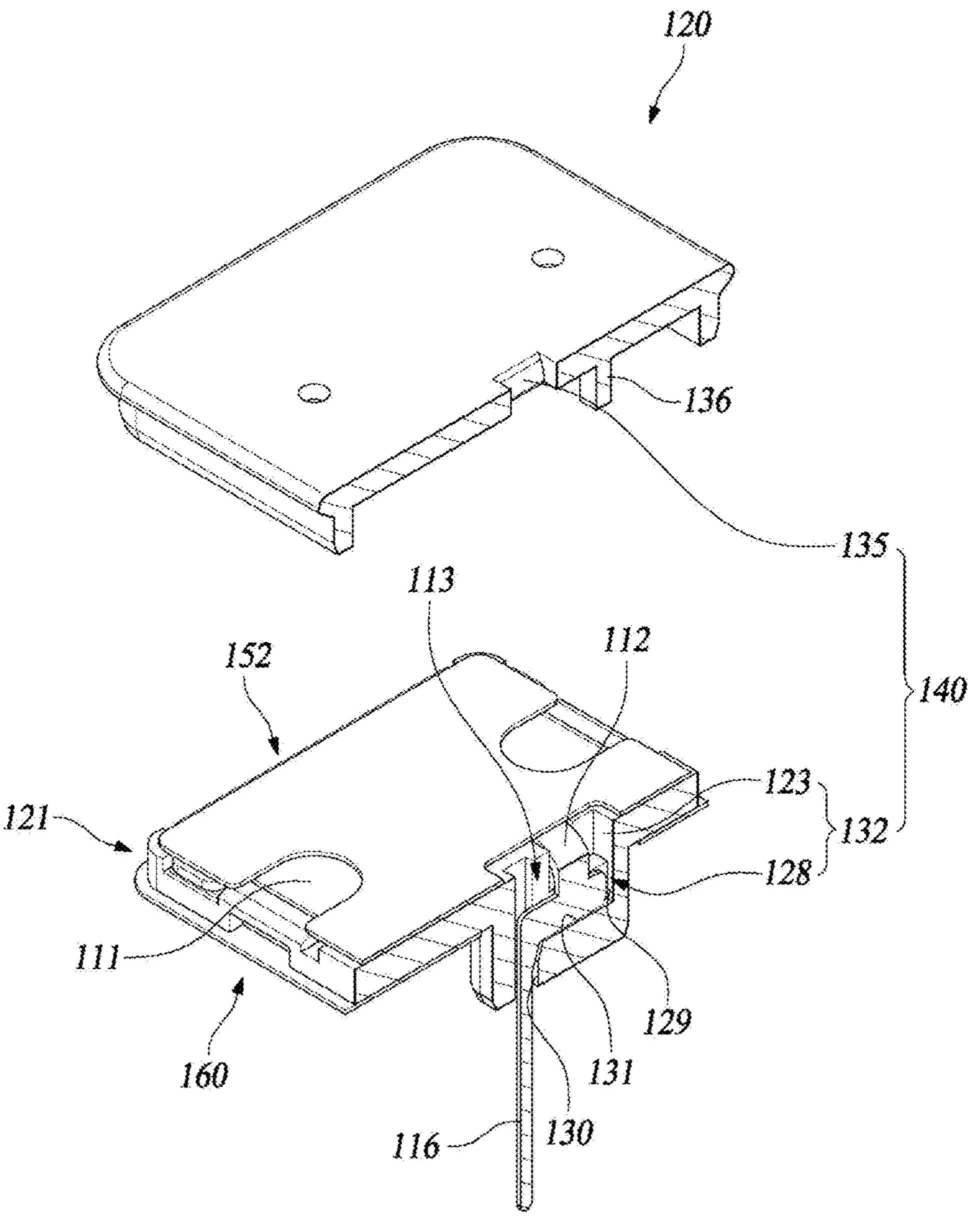
FIG. 6 is a cross-sectional view showing a portion of a sensor unit disassembled.
Figure 7:
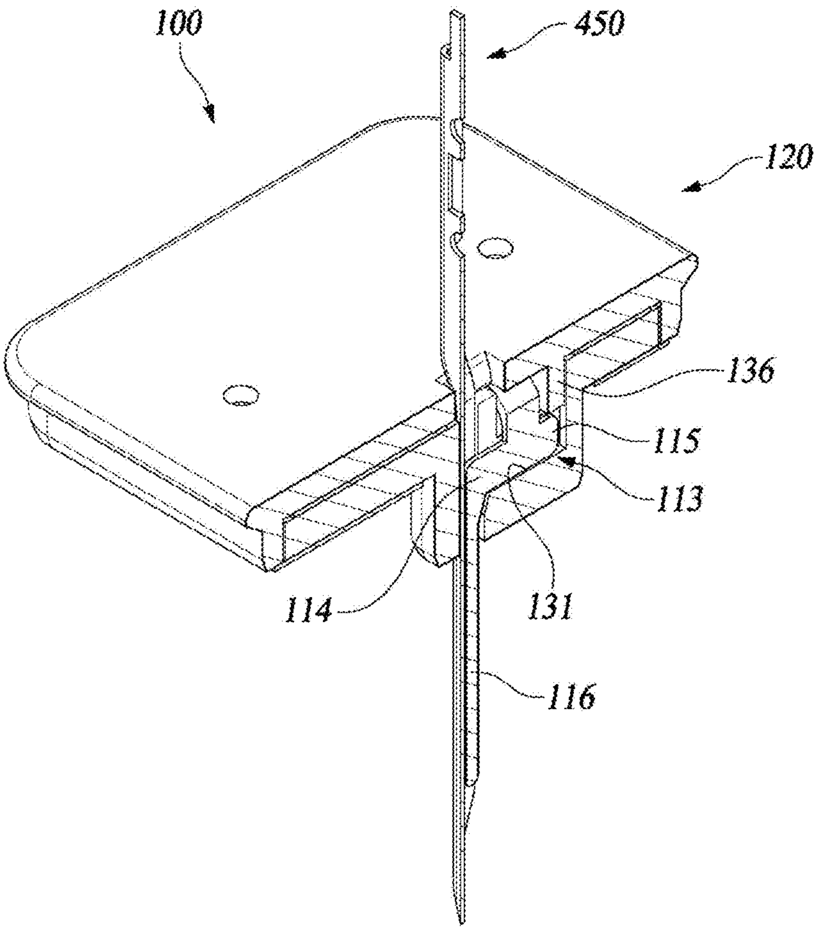
FIG. 7 is a cross-sectional view showing a needle coupled to a sensor unit.

As shown in FIGS. 6 and 7, when the housing cap (134) is coupled to the housing base (121), the retention protrusion (136) is inserted into the housing base hole (132) and comes into contact with the sensor (110). That is, the retention protrusion (136) is arranged so that its end faces the second extension (115) of the middle portion (113) inserted into the housing base hole (132), and may restrain the movement of the middle portion (113) of the sensor (110) so that the middle portion (113) does not lift off the support portion (131). Due to the action of these retention protrusions (136), the insertion portion (116) of the sensor (110) can be stably maintained in a state of protruding from the sensor unit housing (120) by a certain length. And, due to the action of the retention protrusion (136), the insertion portion (116) of the sensor (110) does not retreat from the skin of a user while being inserted into the skin of a user, and can remain inserted at a certain depth into the skin of a user.

Figure 8:
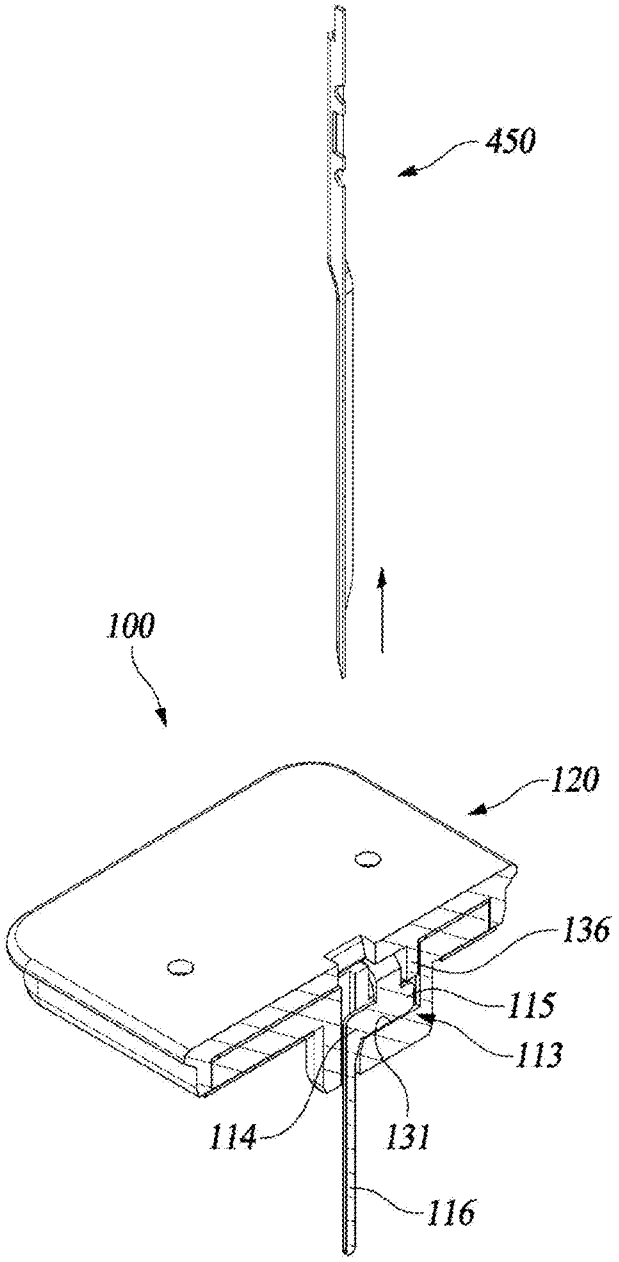
FIG. 8 is a cross-sectional view showing a needle being separated from a sensor unit.
Figure 9:
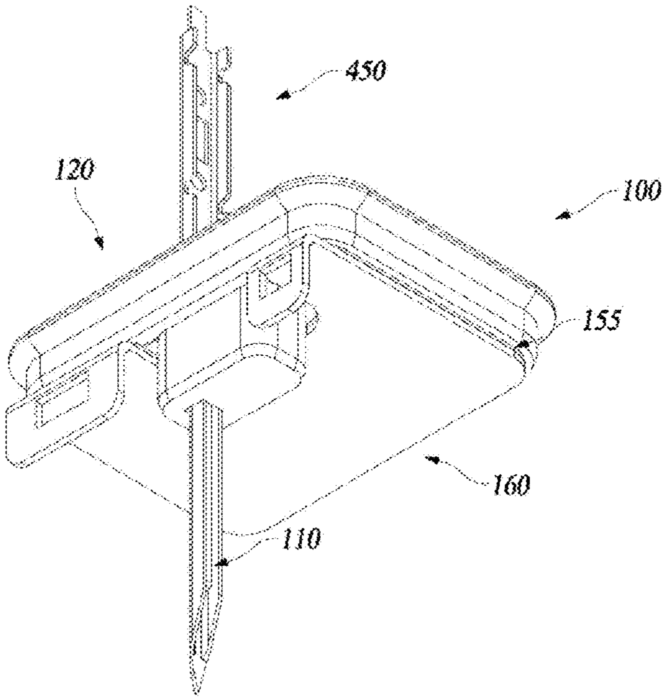
FIG. 9 shows a protective sheet attached to an adhesive layer of a sensor unit.
Figure 10:
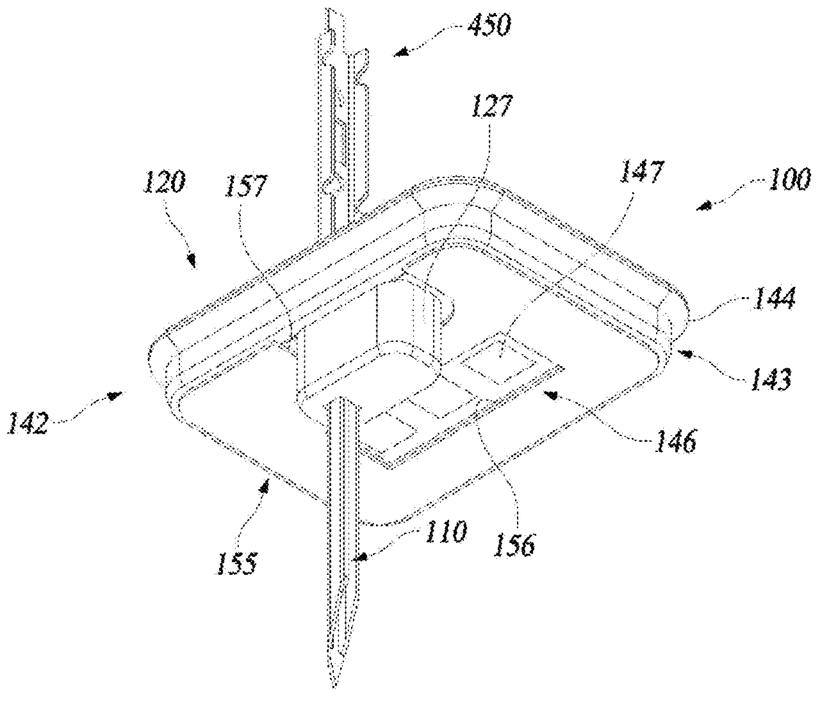
FIG. 10 shows the appearance after the protective sheet is separated from an adhesive layer of a sensor unit.
Figure 11:
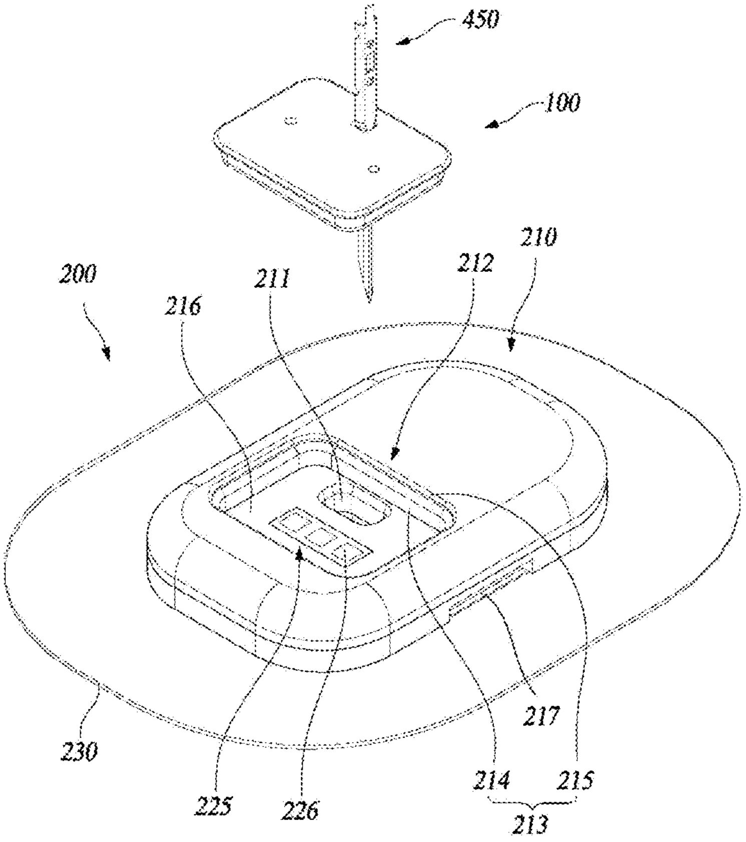
FIGS. 11 and 12 show a sensor unit and a base unit before they are coupled.
Figure 12:
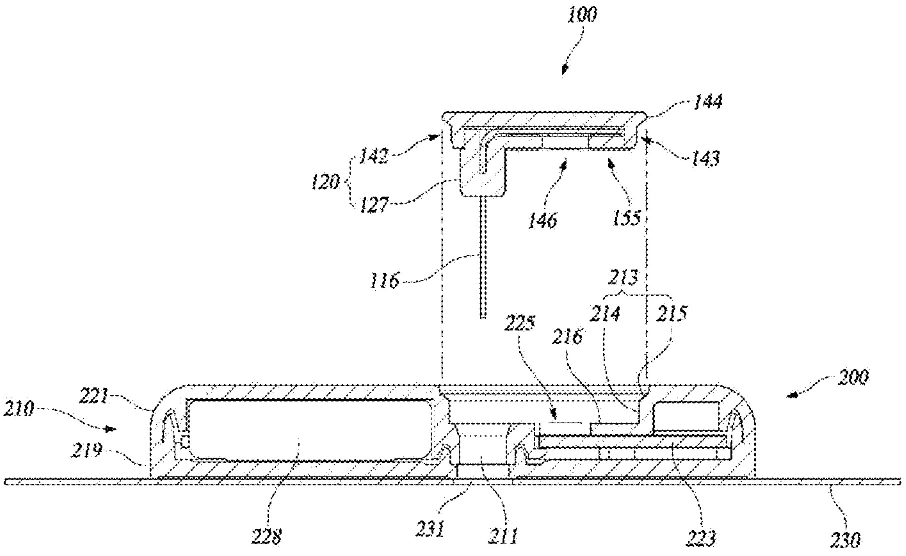
Figure 13:
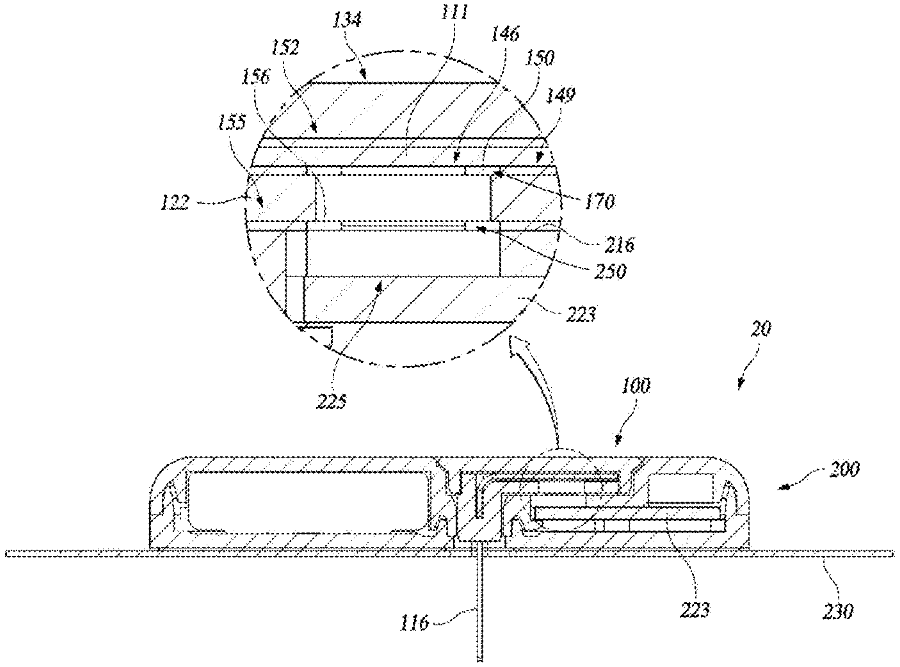
FIG. 13 is a cross-sectional view showing a body attachable unit assembled by coupling a sensor unit and a base unit.

Also, as shown in FIG. 8, after the insertion portion (116) is inserted into the skin of a user together with the needle (450), the retention protrusion (136) prevents the middle portion (113) from moving during the process of the needle (450) coming out of the skin of a user, so that the insertion portion (116) cannot retract in the same direction as the needle (450). Accordingly, it is possible to prevent a problem in which the insertion portion (116) inserted into the skin of a user moves in the direction in which the needle (450) exits the skin of a user during the process of the needle (450) coming out of the skin of a user. In addition, it may prevent the problem of the insertion portion (116) partially coming out of the skin and reducing the measurement accuracy of the sensor (110).

The housing cap (134) forms the housing body (142) together with the base portion (122). That is, the sensor unit housing (120) may be configured to include a housing body (142) and a boss (127) protruding from one side of the housing body (142). The housing body (142) is shaped to fit into the base unit recess (213) of the base unit (200). The housing body (142) includes a body portion (143) provided with a boss (127) and a cover portion (144) that is wider than the body portion (143).

The sensor unit housing (120) is not limited to the configuration shown, and may be changed to various other configurations on which the sensor (110) may be mounted and coupled to the base unit (200). That is, the sensor unit housing (120) includes a housing base (121) and the housing cap (134), but it can be changed to various configurations other than a configuration including a housing body (142) and a boss (127) protruding from the housing body (142).

The sensor unit-electrical contact portion (146) is disposed in the sensor unit housing (120) to be electrically connected to the sensor body (111) of the sensor (110). The sensor unit-electrical contact portion (146) is inserted into the through hole (124) of the base portion (122) and is disposed to vertically penetrate the base portion (122). The sensor unit-electrical contact portion (146) may include a plurality of terminal portions (147) for transmitting electrical signals. Some part of the sensor unit-electrical contact portion (146) is exposed to one surface of the base portion (122) where the sensor body (111) of the sensor (110) is located, and another part is exposed to the other side of the base portion (122), so that the sensor (110) and a base unit-electrical contact portion (225) of the base unit (200) can be electrically connected.

The sensor adhesive portion (149) is disposed between the housing base (121) and the sensor body (111) of the sensor (110) to attach the sensor body (111) to the housing base (121). The sensor adhesive portion (149) has adhesive properties on both sides. That is, one side of the sensor adhesive portion (149) is adhered to the housing base (121), and the other surface of the sensor adhesive portion (149) is adhered to the sensor body (111). A sensor adhesive portion opening (150) is formed in the middle of the sensor adhesive portion (149) to penetrate the sensor adhesive portion (149) in the thickness direction. The sensor body (111) of the sensor (110) is in contact with the sensor unit-electrical contact portion (146) through the sensor adhesive portion opening (150). Therefore, the sensor adhesive portion (149) surrounds a plurality of contact points provided on the sensor body (111) and seals the contact points of the sensor body (111). Additionally, the sensor adhesive portion (149) seals between the sensor body (111) and the sensor unit-electrical contact portion (146), thereby preventing moisture or foreign substances from entering an electrical connection portion (170) between the sensor body (111) and the sensor unit-electrical contact portion (146).

The shape of the sensor adhesive portion (149) is not limited to that shown and can be changed in various ways.

The adhesive pad (152) is disposed between the housing cap (134) and the sensor body (111) of the sensor (110) to attach the sensor body (111) to the housing cap (134). The adhesive pad (152) has adhesive properties on both sides. That is, one side of the adhesive pad (152) is adhered to the housing cap (134), and the other side of the adhesive pad (152) is adhered to the sensor body (111). An adhesive pad groove (153) is formed in the adhesive pad (152) to penetrate the adhesive pad (152) in the thickness direction. The protrusion (137) of the housing cap (134) contacts the sensor body (111) through the adhesive pad groove (153), thereby pressing the sensor body (111) toward the housing base (121).

The shape of the adhesive pad (152) is not limited to that shown and can be changed in various ways.

An adhesive layer (155) is disposed on the surface of the housing base (121). The adhesive layer (155) has adhesive properties on both sides. One side of the adhesive layer (155) is adhered to the housing base (121), and the other side of the adhesive layer (155) is covered with the protective sheet (160). The adhesive layer (155) may be attached to the base unit (200) after the protective sheet (160) is separated. An adhesive layer hole (156) is formed in the middle portion of the adhesive layer (155) to penetrate the adhesive layer (155) in the thickness direction. The sensor unit-electrical contact portion (146) may contact the base unit-electrical contact portion (225) of the base unit (200) through the adhesive layer hole (156). Therefore, the adhesive layer (155) seals between the sensor unit-electrical contact portion (146) and the base unit-electrical contact portion (225), thereby preventing moisture or foreign substances from entering the electrical connection portion (250) between the sensor unit (100) and the base unit (200). An adhesive layer opening (157) is formed on one side of the adhesive layer (155) to penetrate the adhesive layer (155) in the thickness direction. The adhesive layer (155) is attached to the housing base (121) such that the sensor unit-electrical contact portion (146) is located inside the adhesive layer hole (156) and the boss (127) is inserted into the adhesive layer opening (157).

The shape of the adhesive layer (155) is not limited to that shown and can be changed in various ways.

The protective sheet (160) covers and protects the adhesive layer (155). The protective sheet (160) is made of a material that is detachably attached to the adhesive layer (155). If the adhesive layer (155) is left exposed to the air for a long time, the adhesiveness of the adhesive layer (155) may deteriorate. The protective sheet (160) covers the adhesive layer (155) to prevent the problem of reducing of adhesiveness of the adhesive layer (155), and it facilitates handling of the sensor unit (100) by an operator during the manufacturing process of the sensor unit (100) or the process of assembling the sensor unit (100) to the applicator (30). The protective sheet (160) includes a protection portion (161) adhered to the adhesive layer (155) and a wing portion (164) extending from an edge of the protection portion (161). A protective sheet opening (162) is formed on one side of the protection portion (161) to penetrate the protection portion (161) in the thickness direction. The protective sheet (160) is attached to the adhesive layer (155) such that the boss (127) is inserted into the protective sheet opening (162). The length of the wing portion (164) is longer than the length of the protection portion (161). A protective sheet groove (165) is formed in the wing portion (164) to penetrate the wing portion (164) in the thickness direction. The wing portion (164) may extend by a certain length from the edge of the sensor unit housing (120) and be coupled to the removing unit (500) of the applicator (30).

The shape of the protective sheet (160) is not limited to that shown and can be changed in various ways.

The sensor unit (100) is mounted on the applicator (30) with the protective sheet (160) attached to the adhesive layer (155). The protective sheet (160) may be separated from the adhesive layer (155) by a removing unit (600) of the applicator (30) before the sensor (110) is inserted into the skin of a user. The sensor unit (100) moves toward the base unit (200) with the protective sheet (160) separated and is coupled to the base unit (200).

As shown in FIG. 1 and FIGS. 11 to 13, the base unit (200) includes a base unit housing (210) to which the sensor unit (100) is coupled, and electronic components installed inside the base unit housing (210). The electronic component may include a circuit board (223), a base unit electrical contact portion (225) in contact with the sensor unit-electrical contact portion (146) of the sensor unit (100), a battery (228), etc. The circuit board (223) may be equipped with a processor chip for processing signals, a communication chip for wireless communication with the external terminal 5, etc.

The base unit housing (210) is provided with an insertion hole (211) through which the insertion portion (116) of the sensor (110) and the needle (450) can pass, and a mounting portion (212) in which the sensor unit housing (120) is coupled. The mounting portion (212) includes a base unit recess (213) and a contact surface (216) provided inside the base unit recess (213). The insertion hole (211) is shaped so that the boss (127) of the sensor unit (100) can be fitted and is disposed inside the base unit recess (213). The contact surface (216) may be flat so that the adhesive layer (155) of the sensor unit (100) can be stably adhered. The base unit recess (213) includes a first recess (214) connected to the insertion hole (211), and a second recess (215) that is located farther from the insertion hole (211) than the first recess (214) and is connected to the first recess (214). The second recess (215) is wider than the first recess (214). The first recess (214) can be made in a shape corresponding to the body portion (143) of the sensor unit housing (120), and the second recess (215) can be made in a shape corresponding to the cover portion (144) of the sensor unit housing (120). Therefore, the sensor unit housing (120) can be fitted into the base unit recess (213) and maintain a stable coupling state with the base unit housing (210). In addition, since the sensor unit housing (120) is stably fitted and coupled to the base unit housing (210), moisture or foreign substances cannot easily enter the gap between the sensor unit housing (120) and the base unit housing (210). A housing groove (217) is formed on the outer edge of the base unit housing (210). A portion of a locking hook for detachably fixing the base unit (200) to the applicator (30) may be inserted into the housing groove (217).

The base unit-electrical contact portion (225) is arranged on the mounting portion (212) and contacts the sensor unit-electrical contact portion (146) of sensor unit (100) when sensor unit (100) is coupled to the base unit (200). The base unit-electrical contact portion (225) is electrically connected to the circuit board (223) and is installed in the base unit housing (210) so that a portion is exposed to the base unit recess (213). The base unit-electrical contact portion (225) may include a plurality of terminal portions (226) for transmitting electrical signals. The terminal portion (226) may electrically connect the sensor unit-electrical contact portion (146) and the circuit board (223) by contacting the terminal portion (147) of the sensor unit (100).

As shown, the base unit housing (210) may include a lower housing (219) and an upper housing (221) that covers the upper part of the lower housing (219), but its shape may be changed in various ways.

An adhesive portion (230) is provided on the surface of the base unit housing (210). The adhesive portion (230) is attached to the surface of the lower housing (219) to adhere the base unit housing (210) to the skin of a user. In the middle of the adhesive portion (230), an adhesive hole (231) through which the insertion portion (116) of the sensor (110) and the needle (450) can pass is formed to penetrate the adhesive portion (230) in the thickness direction.

The adhesive portion (230) may be covered and protected with a protective sheet. The protective sheet covering the adhesive portion (230) may be removed during the process of attaching the base unit (200) to the skin of a user.

The sensor unit (100) and the base unit (200) are installed in the applicator (30) in a separated state, and are coupled to each other in the process of operating the applicator (30) to insert the sensor (110) into the skin of a user, forming the body attachable unit (20). The sensor unit (100) may be mounted on the applicator (30) while the needle (450) coupled, and moved toward the base unit (200) with the needle (450) coupled thereto to be coupled to the base unit (200). After the sensor unit (100) is coupled to the base unit (200), the needle (450) is separated from the sensor unit (100), and only the body attachable unit (20) remains on the skin of a user.

Figure 14:
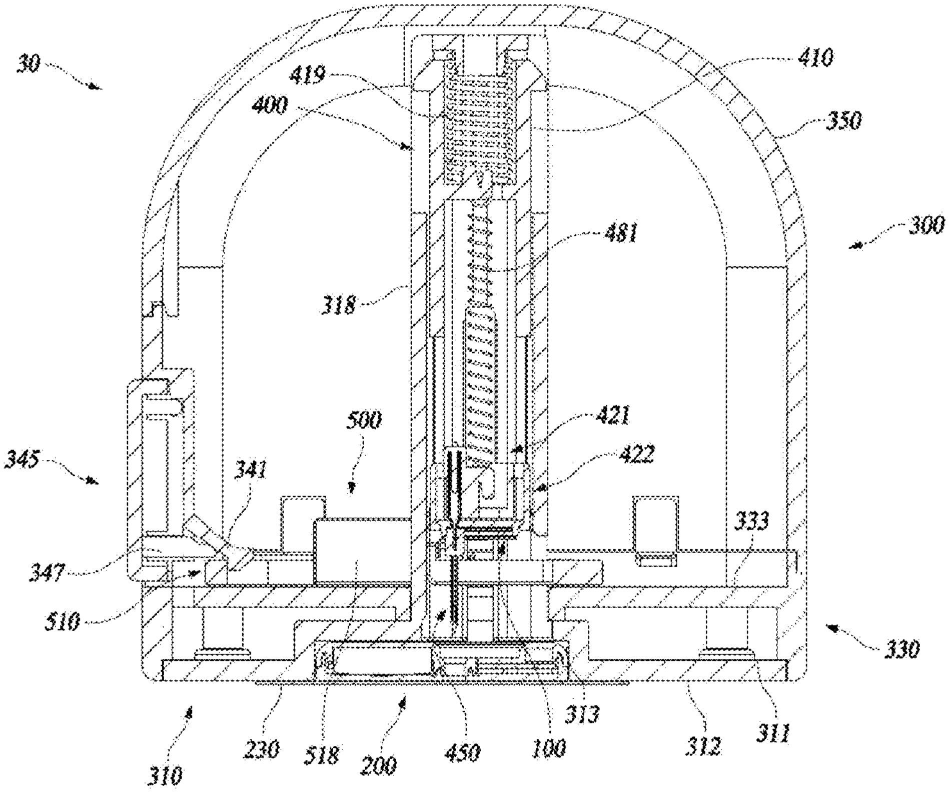
FIG. 14 is a cross-sectional view taken along line I-I in FIG. 3.
Figure 15:
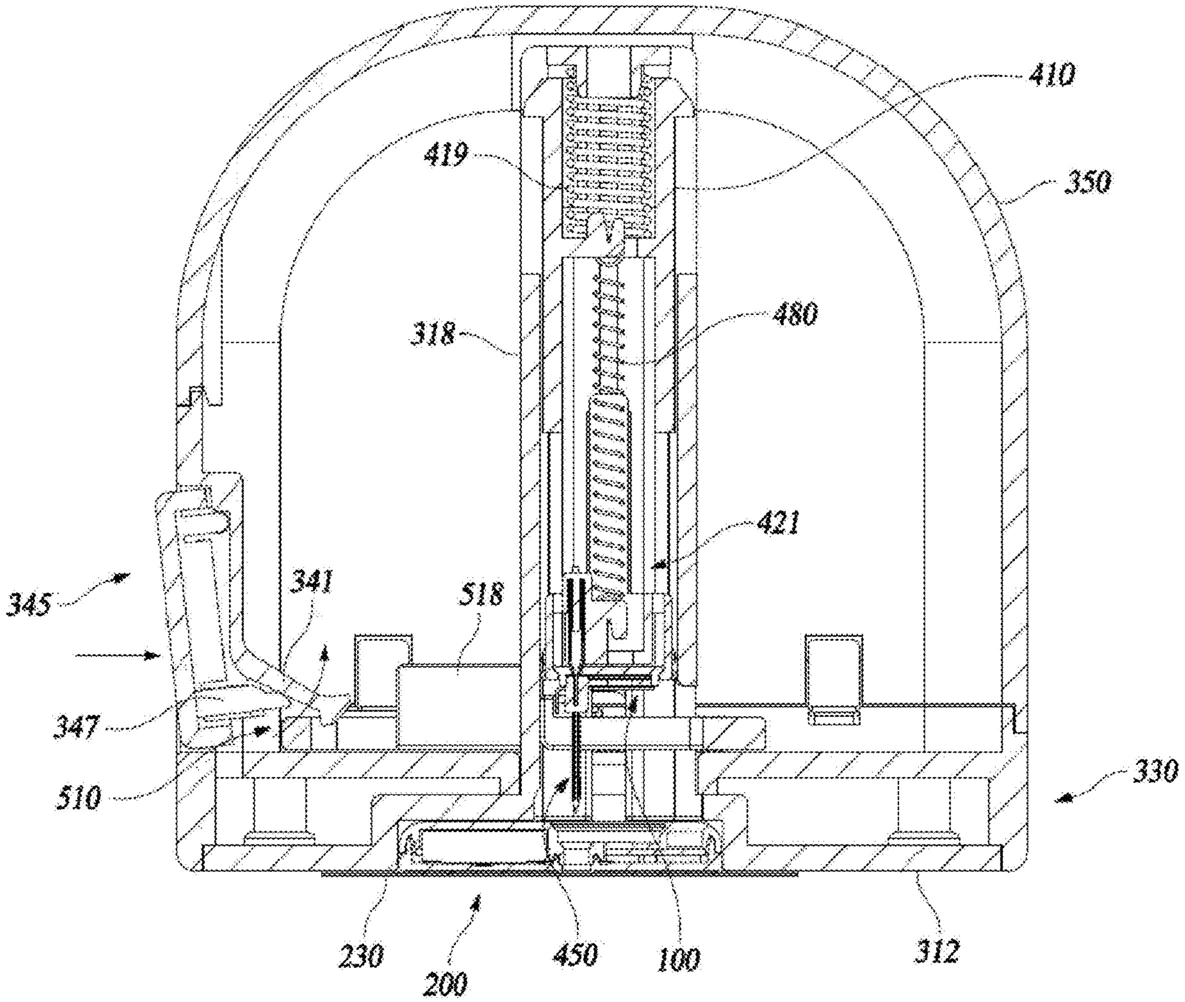
FIG. 15 shows a view in which the operating member of the applicator biases the stopper to be disengaged from the moving member.

Referring to FIGS. 14 and 15, the applicator (30) operates with the sensor unit (100) and the base unit (200) mounted, thereby coupling the sensor unit (100) and the base unit (200) and can attach the body attachable unit (20) in which the sensor unit (100) and the base unit (200) are coupled to the skin of a user. The sensor unit (100) and the base unit (200) are spaced apart from each other and are respectively mounted on the applicator (30). The applicator (30) is separated from the body attachable unit (20) after attaching the body attachable unit (20) to the skin of a user, and the body attachable unit (20) remains attached to the skin of a user by the adhesive portion (230).

The applicator (30) includes an applicator body (300) to which the base unit (200) is detachably coupled, an insertion unit (400) that moves the sensor unit (100) to insert the sensor (110) into the skin of a user, and removing unit (500) for removing the protective sheet (160) of the sensor unit (100). The insertion unit (400) may move the sensor unit (100) from a first position spaced apart from the base unit (200) by a preset distance to a second position coupled with the base unit (200). The sensor unit (100) and a top case (350) which is coupled to the middle frame (330) and covers the upper part of the middle frame (330).

The applicator body (300) includes a base frame (310) on which the insertion unit (400) is installed, a middle frame (330) disposed on the base frame (310) and on which the removing unit (500) is installed, and a top case (350) that is coupled to and covers the upper part of the middle frame (330).

The base frame (310) includes a frame base portion (311) having a bottom portion (312) that can be in contact with the skin of a user, and a column portion (318) which protrudes from the frame base portion (311) and accommodates the sensor unit (100) and the insertion unit (400). The bottom portion (312) of the frame base portion (311) is provided with a recess (313) into which the base unit (200) is mounted. The base unit (200) is detachably coupled to the recess (313) so that the adhesive portion (230) can face the skin of a user and placed in a second position spaced apart from the sensor unit (100). A through hole (314) is formed in the frame base portion (311) to penetrate the frame base portion (311) in the thickness direction. A pair of through holes (314) are provided on both sides of the column portion (318) with the column portion (318) interposed therebetween. A support portion (316) to which the locking hook (325) is coupled is provided at the top of the through hole (314).

The middle frame (330) includes a stage (333) disposed on the frame base portion (311). The stage (333) supports the moving member (510) of the removing unit (500) to move linearly. An opening into which the column portion (318) is inserted is formed in the middle of the stage (333), so that the column portion (318) can protrude above the stage (333). The middle frame (330) includes a stopper (341) that engages the moving member (510) to restrict the movement of the moving member (510), and an operating member (345) capable of operating the insertion unit (400) and the removing unit (500). The stopper (341) may be released by the operating member (345) so that the binding force on the moving member (510) may be removed. The operating member (345) is pivotally coupled to the middle frame (330) and has a pressing protrusion (347) capable of pressing the stopper (341). When a user presses the operating member (345), the pressing protrusion (347) of the operating member (345) may press the stopper (341). At this time, the stopper (341) may be elastically deformed and disengaged from the moving member (510).

The top case (350) is coupled with the middle frame (330) and covers the middle frame (330) and the upper portions of the base frame (310).

The insertion unit (400) is installed on the applicator body (300) to associate with the moving member (510) of the removing unit (500) to move the sensor unit (100) from the first position to the second position, and the sensor (110) can be inserted into the skin of a user. The insertion unit (400) includes a plunger (410) installed movably on the middle frame (330) and a needle assembly (421) having a needle (450) that can be moved with the plunger (410) and inserted into the skin of a user.

The plunger (410) is installed inside the column portion (318) to be movable from the first position to the second position. The plunger (410) is fixed in the first position by partially engaging the moving member (510), and can move to the second position when the engagement is released from the moving member (510). The plunger (410) moves by receiving a moving force from the elastic member (419). The elastic member (419) may apply elastic force to the plunger (410) in a direction moving from the first position to the second position.

the needle assembly (421) includes the carrier (422) to which the sensor unit (100) is detachably coupled, and a needle (450) coupled to the carrier (422) penetrating the sensor unit (100). In a state in which the needle (450) is coupled to the sensor unit (100), the needle (450) advance from the first position to the second position together with the sensor unit (100) to be inserted into the skin of a user, and then may retreat with the carrier (422) in the second position and be separated from the skin of a user and the sensor unit (100).

The carrier (422) is coupled to the plunger (410) to enable relative movement. A portion of the carrier (422) engages the plunger (410) so as to move with the plunger (410) from the first position to the second position. Then, the carrier (422) is disengaged from the plunger (410) in the second position and may retreat in a direction away from the sensor unit (100).

The carrier (422) can be moved relative to the plunger (410) by the elastic member (481). The elastic member (481) applies elastic force to the carrier (422) in a direction away from the base unit (200). The carrier (422) may move to the second position to couple the sensor unit (100) to the base unit (200) and then be disengaged from the plunger (410) and retreat in a direction away from the base unit (200).

The needle (450) is fixed to the carrier (422) and can move from the first position to the second position while coupled to the sensor unit (100). The needle (450) has a sharp tip so as to pierce the skin of a user and be smoothly inserted into the skin of a user. When the sensor unit (100) moves to the second position, the needle (450) penetrates the skin of a user before the sensor (110) and allows the sensor (110) to be stably inserted into the skin. The needle (450) is separated from the skin of a user after the sensor (110) is inserted into the skin of a user.

Before the sensor unit (100) reaches the second position and is coupled to the base unit (200), the removing unit (500) is installed on the applicator body (300) to separate the protective sheet (160) of the sensor unit (100) from the adhesive layer (155). The removing unit (500) includes a moving member (510) installed movably on the middle frame (330) to be coupled to the protective sheet (160). The moving member (510) is arranged to move linearly on the stage (333) of the middle frame (330). The moving member (510) includes a support portion (518) for supporting the plunger (410).

The moving member (510) is installed to move in a direction that is approximately perpendicular to the direction in which the sensor unit (100) moves from the first position to the second position. The moving member (510) may pull the protective sheet (160) to be separated from the adhesive layer (155) by moving while coupled to the protective sheet (160). Specifically, in a state in which the protective sheet (160) covers the adhesive layer (155) by the elastic member, the moving member (510) can move from a third position where the protective sheet is coupled to a fourth position where the protective sheet (160) is removed from the adhesive layer. The moving member (510) fixes the plunger (410) at the first position by coming into contact with the plunger (410) located in the first position at the third position, and when the moving member moves to the fourth position, it deviates from the plunger (410) so that the plunger 410 can move to the second position.

Figure 17:
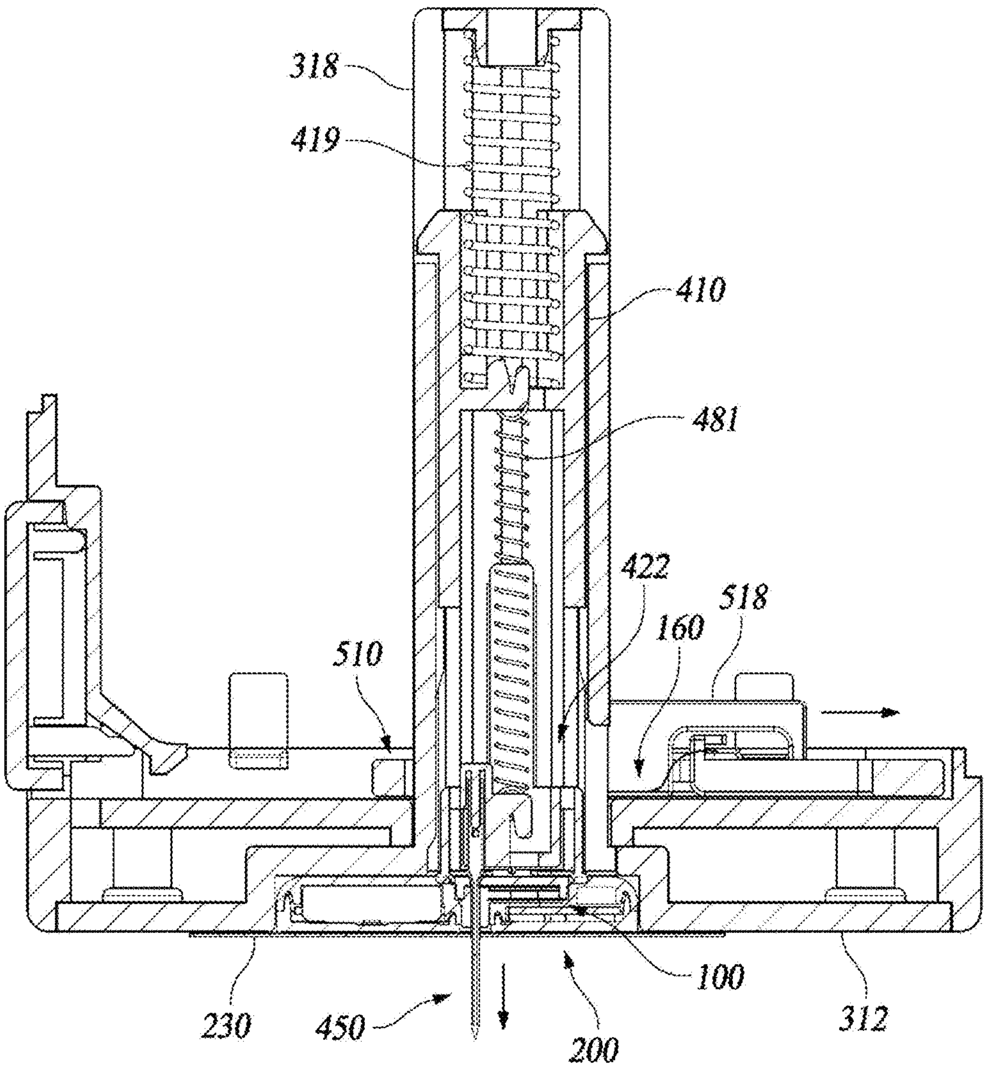
Figure 18:
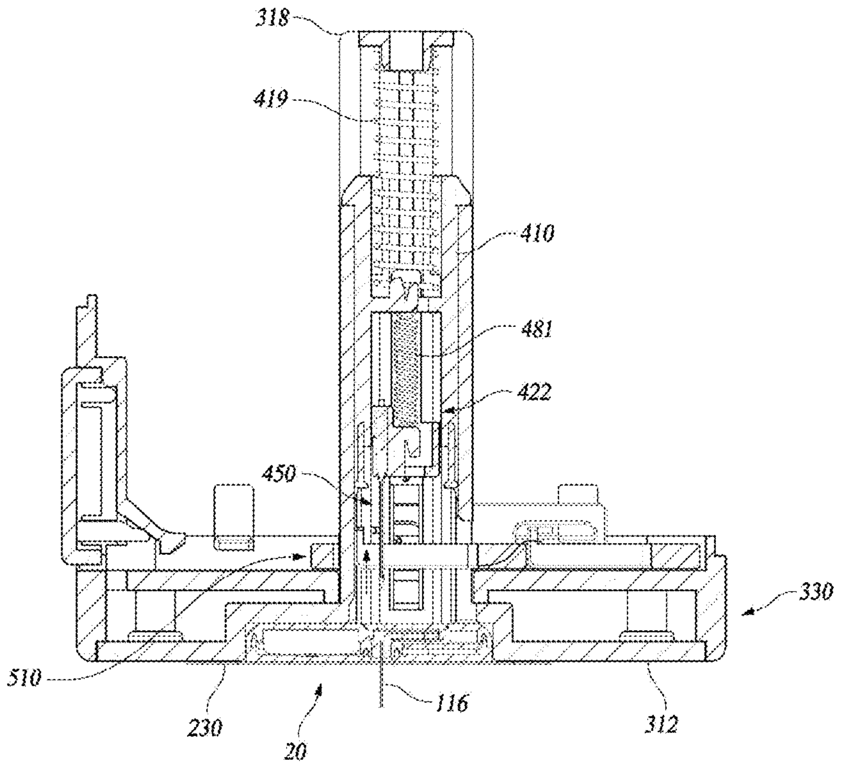

Hereinafter, with reference to FIGS. 16 to 18, a method of attaching the body attachable unit (20) according to an embodiment of the present disclosure to the skin of a user using the applicator (30) will be described.

Figure 16:
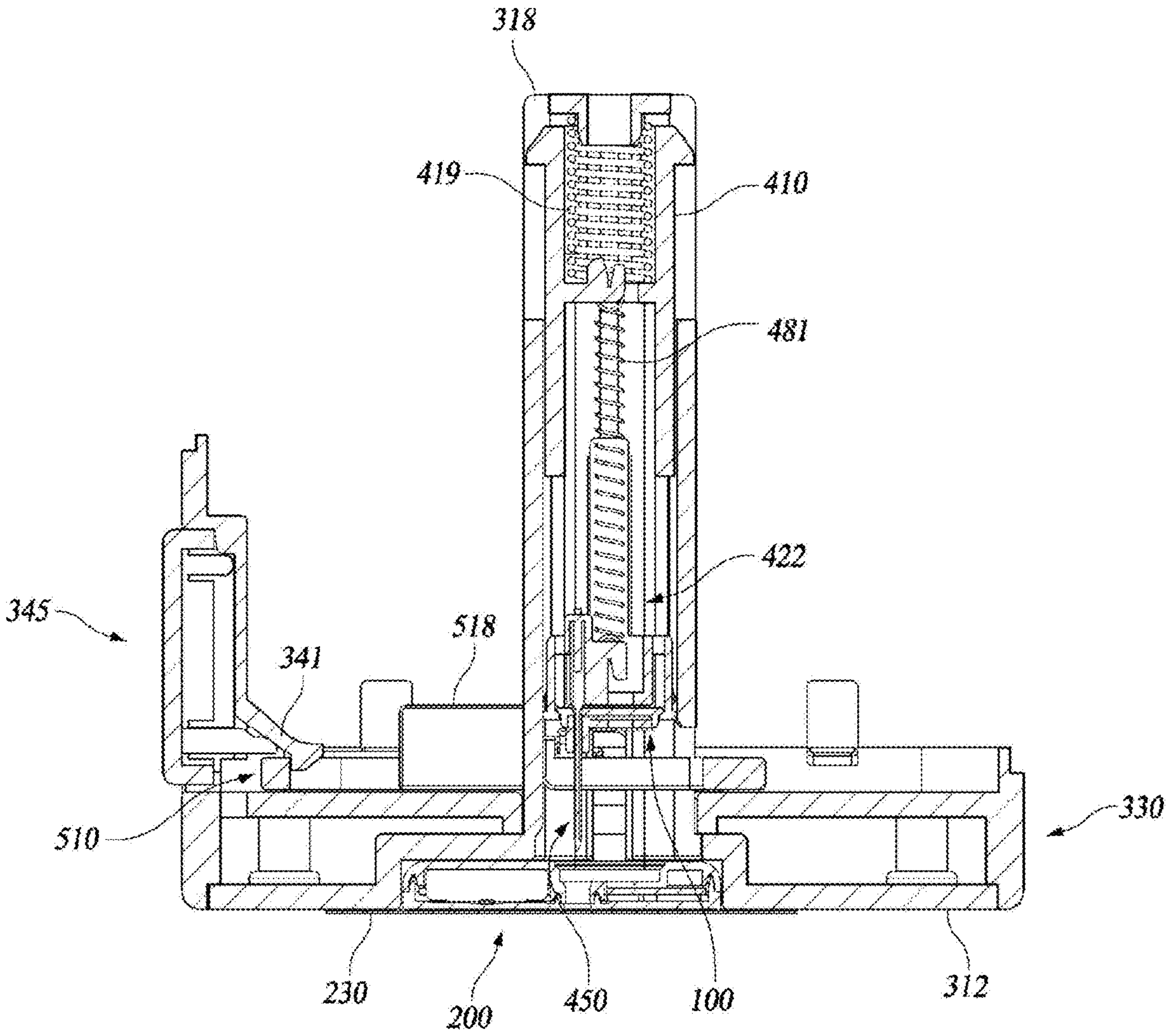
FIGS. 16 to 18 show a process in which the sensor of the sensor unit is inserted into the skin of a user by an applicator.

Referring to FIG. 16, first, the bottom portion (312) of the applicator (30) is placed on the skin of a user so that the base unit (200) is attached to the skin of a user by the adhesive portion (230). Before the operating member (345) is manipulated, the sensor unit (100) coupled to the carrier (422) is positioned in the first position in a state in which the protective sheet (160) covers the adhesive layer (155). And the moving member (510) is located in the third position engaging with the stopper (341).

Thereafter, when the operating member (345) is pressed, the moving member (510) is disengaged from the stopper (341) and the moving member (510) is moved to the fourth position by the moving member driver (522). As shown in FIG. 17, as the moving member (510) moves to the fourth position, the protective sheet (160) is pulled by the moving member (510) and separated from the adhesive layer (155). Then, the plunger (410) moves away from the moving member (510) and moves to the second position by the plunger driver (418). At this time, the insertion portion (116) of the sensor (110) and needle (450) are inserted into the skin of a user, and the sensor unit (100) from which the protective sheet (160) is separated is attached to the base unit (200) by the adhesive layer (155), so that the body attachable unit (20) is assembled.

After the plunger (410) moves and the insertion portion (116) and the needle (450) are inserted into the skin of a user, the carrier (422) is disengaged from the plunger (410) and the carrier (422) is moved in a direction away from the skin of a user by the elastic member (481). At this time, the needle (450) comes out of the skin of a user and the body attachable unit (20) remains attached to the skin of a user by the adhesive portion (230).

After the insertion portion (116) of the sensor (110) is inserted into the skin, in the process of the needle (450) coming out of the skin of a user, the retention protrusion (136) of the sensor unit housing (120) comes into contact with the middle portion (113) of the sensor (110) and restricts the movement of the insertion portion (116). Accordingly, the insertion portion (116) cannot retreat in the same direction as the needle (450) and can remain stably inserted into the skin.

The body attachable unit (20) attached to the skin of a user and separated from the applicator (30) can measure the biometric information of a user and transmit the measurement information to an external terminal (5) or the like.

As described above, in the sensor unit (100) according to the present disclosure, the movement of the sensor (110), which is inserted into the skin of a user with the needle, to retreat from the skin by the retention protrusion (136) of the sensor unit housing (120) is limited. Therefore, during the process of the needle (450) being separated from the skin of a user, the sensor (110) can remain stably inserted into the skin without being affected by the movement of the needle (450).

In addition, Even if the sensor unit (100) according to the present disclosure, is used attached to the skin for a long time, biometric information can be stably measured while the sensor (110) is stably inserted into the skin.

Figure 19:
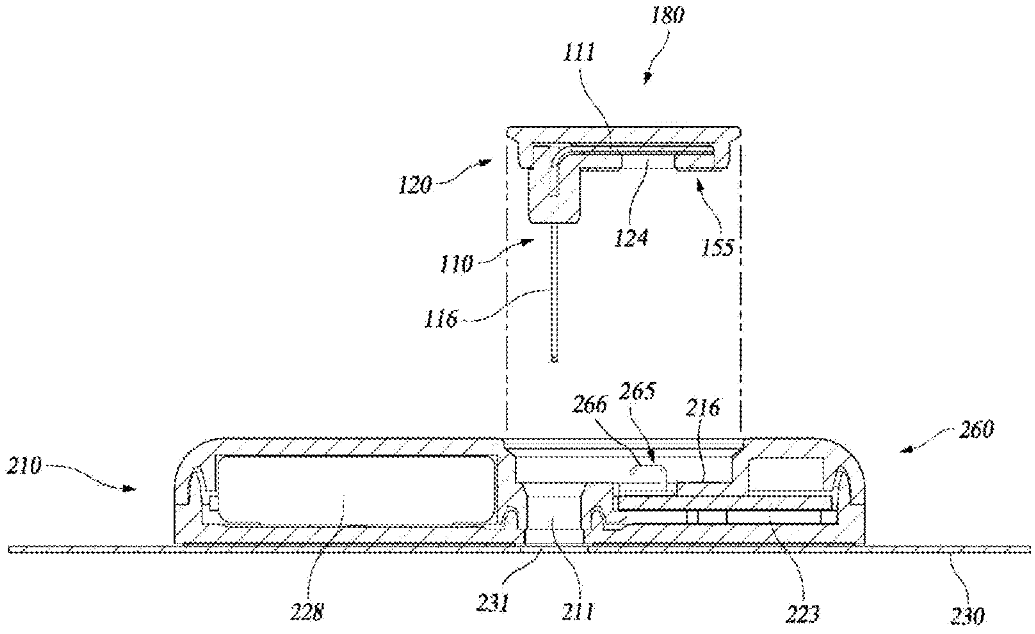
FIGS. 19 and 20 show another embodiment of the sensor unit and the base unit.
Figure 20:
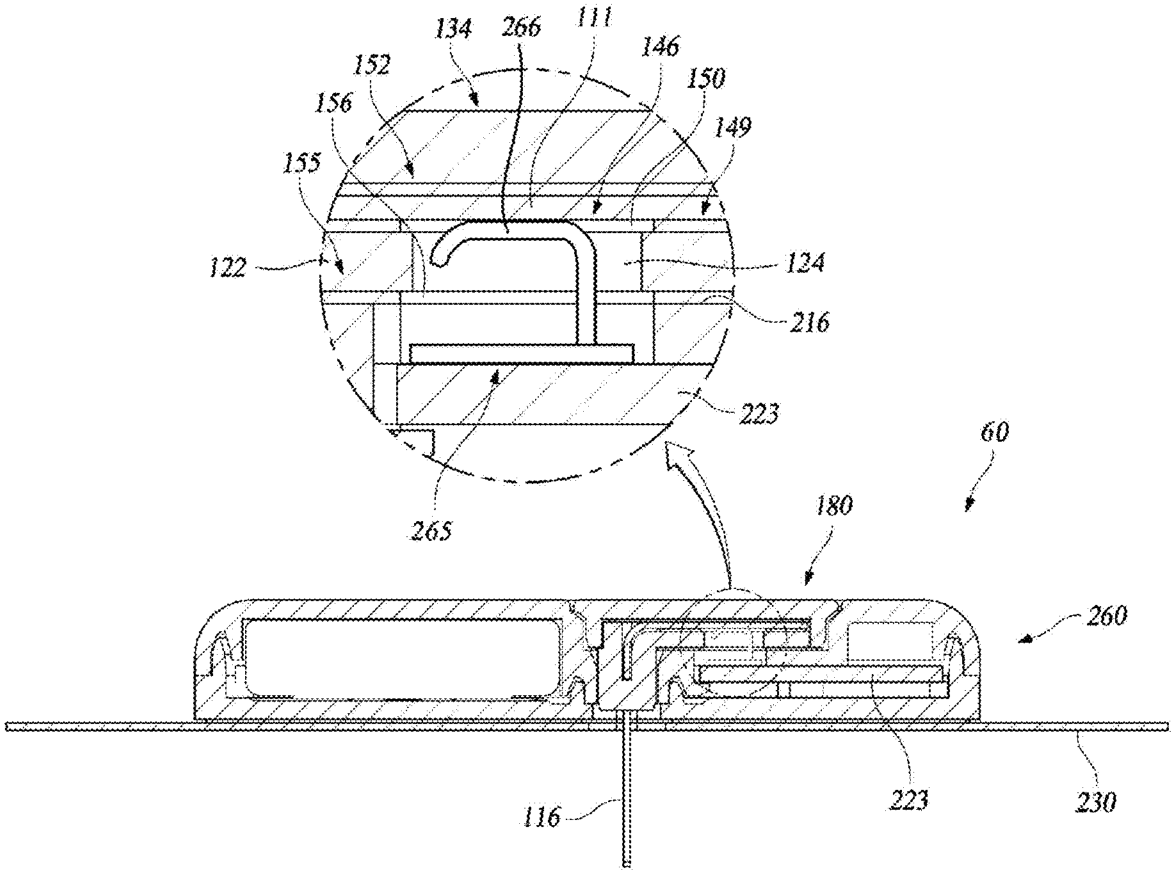

Meanwhile, FIGS. 19 and 20 show other embodiments of the sensor unit and base unit.

As shown in FIGS. 19 and 20, the sensor unit (180) includes the sensor (110) inserted into the skin of a user, the sensor unit housing (120) to which the sensor (110) is coupled, the sensor adhesive portion (149) and adhesive pad (152) for fixing the sensor (110) to the sensor unit housing (120), the adhesive layer (155) provided on the sensor unit housing (120) to be attached to the base unit (260) and the protective sheet covering the adhesive layer (155). The sensor unit (180) has a configuration in which the sensor unit-electrical contact portion for electrically connecting the sensor (110) to the base unit (260) is omitted.

The base unit (260) includes the base unit housing (210) to which the sensor unit (180) is coupled, the circuit board (223) installed inside the base unit housing (210), the base unit-electrical contact portion (265) electrically connected to the sensor (110) of the sensor unit (180) and a battery (228). Base unit-electrical contact portion (225) contact sensor (110) when sensor unit (180) is coupled to base unit (260). The base unit-electrical contact portion (225) is electrically connected to the circuit board (223), and a portion of the base unit-electrical contact portion (225) may protrude from the contact surface (216) to contact the sensor (110). The base unit-electrical contact portion (225) may include a plurality of terminal portions (266) that each contact a plurality of contact points (not shown) provided on the sensor body (111) of the sensor (110). The terminal portion (266) may electrically connect the sensor (110) and the circuit board (223) by contacting the contact points of the sensor body (111). The terminal portion (266) may be formed to be elastically deformed when in contact with the sensor body (111) so as to stably contact the sensor body (111).

The sensor unit (180) is attached to the base unit (260) by the adhesive layer (155), thereby forming a body attachable unit (60) together with the base unit (260). When the sensor unit (180) is coupled with the base unit (260), the base unit-electrical contact portion (265) passes through the adhesive layer hole (156), the through hole (124), and the sensor adhesive hole opening (150) and comes into contact with the sensor body (111) of the sensor (110). Accordingly, the sensor (110) may be electrically connected to the base unit (260) through the base unit-electrical contact portion (265). At this time, the adhesive layer (155) seals between the sensor (110) and the base unit-electrical contact portion (265) to prevent moisture or foreign substances from entering the electrical connection portion between the sensor unit (180) and the base unit (260).

In order to electrically connect the sensor (110) and the base unit (260), the specific configuration, number, and location of the base unit-electrical contacts provided in the base unit (260) may be changed in various ways.

Although the present disclosure has been described above with preferred examples, the scope of the present disclosure is not limited to the configurations described and shown above.

For example, in the drawing, it is shown that the sensor unit (110) is coupled with the base unit (200), which includes electronic components, and attached to the skin of a user, but the sensor unit may be configured to include a sensor and electronic components, which is electrically connected to the sensor. Electronic components included in the sensor unit may include a circuit board that is electrically connected to the sensor, a process chip installed on the circuit board that converts biometric information measured by the sensor into an electrical signal, a communication chip for communication with the outside, and a battery. This sensor unit is coupled to the needle and moves from the first position to the second position so that the sensor can be inserted into the skin of a user. The sensor unit is attached to the skin of a user by an adhesive layer in a state in which the sensor is inserted into the skin of a user, measures biometric information, and transmits a measurement signal to an external terminal, etc.

Additionally, as another exemplary embodiment, the base unit may be configured to simply support the sensor unit so that the sensor unit is not separated from the skin of a user. In this case, a separate electronic unit that can process biometric information measured by the sensor unit and transmit it to an external terminal may be detachably coupled to the base unit. A separate electronic unit may be coupled to the base unit to be electrically connected to the sensor unit after the sensor unit is coupled to the base unit. A body attachable unit including such a base unit may be used by coupling a separate electronic unit.

Although the present disclosure has been shown and described in connection with preferred embodiments for illustrating the principles of the disclosure, the disclosure is not limited to the construction and operation as shown and described. Rather, those skilled in the art will understand that numerous changes and modifications can be made to the present disclosure without departing from the concept and scope of the attached registration claims.

What is claimed is:

1. A sensor unit for measuring biometric information of a user by being attached to skin of a user, the sensor unit comprising;

a sensor comprising a sensor body, an insertion portion connected to the sensor body configured to be inserted into the skin of the user, and a middle portion connecting the sensor body and the insertion portion;

a housing base having a housing base hole through which the insertion portion passes, and supporting the sensor body;

a housing cap coupled to the housing base and covering the sensor body; and a retention protrusion protruding from the housing cap configured to be contacted with the middle portion to prevent movement of the insertion portion retreating toward the housing cap, wherein, the middle portion has a wider width than the insertion portion, and the middle portion and the insertion portion configured to be disposed on a plane different from the sensor body, respectively.

2. The sensor unit according to claim 1, wherein the housing base has a support portion disposed inside the housing base hole to support the middle portion.

3. The sensor unit according to claim 2, wherein:

the housing base comprises a base portion supporting the sensor body and a boss protruding from the base portion, and the housing base hole is formed to penetrate the boss in the base portion, and the support portion is disposed inside the boss.

4. The sensor unit according to claim 1, wherein:

the sensor comprises a connection portion connecting the sensor body and the middle portion, the middle portion has a first extension portion protruding from one side of the connection portion, and a second extension portion protruding from the extension portion in a direction opposite to a direction in which the first extension portion protrudes from the connection portion, the insertion portion is connected to the first extension portion, and the retention protrusion is arranged to contact the second extension portion.

5. The sensor unit according to claim 1, wherein the housing cap has a protrusion pressing the sensor body toward the housing base by being contacted with the sensor body.

6. The sensor unit according to claim 1, further comprising an adhesive pad interposed between the sensor body and the housing cap to adhere the sensor body and the housing cap.

7. The sensor unit according to claim 1, further comprising a sensor adhesive portion interposed between the sensor body and the housing base to attach one surface of the sensor body to the housing base, wherein the sensor adhesive portion has a sensor adhesive portion opening, the sensor body has a contact point disposed in the sensor adhesive portion opening for electrical connection, and the sensor adhesive portion seals the contact point by surrounding the contact point.

* * * * *